(12) United States Patent
Kozikowski

(10) Patent No.: US 6,599,940 B2
(45) Date of Patent: Jul. 29, 2003

(54) SYNTHESIS OF 2-HYDROXYMETHYLGLUTAMIC ACID AND CONGENERS THEREOF

(75) Inventor: Alan P. Kozikowski, Princeton, NJ (US)

(73) Assignee: Georgetown University, Washington, DC (US)

(*) Notice: Subject to any disclaimer, the term of this patent is extended or adjusted under 35 U.S.C. 154(b) by 0 days.

(21) Appl. No.: 09/952,325

(22) Filed: Sep. 13, 2001

(65) Prior Publication Data

US 2002/0147362 A1 Oct. 10, 2002

Related U.S. Application Data

(60) Provisional application No. 60/232,275, filed on Sep. 13, 2000.

(51) Int. Cl.$^7$ ............... A61K 31/195; C07C 229/00; C07C 323/00
(52) U.S. Cl. ............. 514/561; 514/562; 514/563; 514/564; 514/566; 560/151; 560/152; 560/155; 560/169; 560/171; 562/557; 562/571; 562/573
(58) Field of Search ................. 560/155, 169, 560/171, 151, 152; 562/571, 573, 557; 514/561, 563, 564, 566, 562

(56) References Cited

U.S. PATENT DOCUMENTS

| | | | |
|---|---|---|---|
| 4,935,534 A | * | 6/1990 | Scholl |
| 5,190,922 A | | 3/1993 | Luly et al. ............ 514/18 |
| 5,362,899 A | | 11/1994 | Campbell ............ 558/108 |
| 5,686,565 A | | 11/1997 | Kyle et al. ............ 530/328 |
| 5,780,589 A | | 7/1998 | Lazarus et al. ......... 530/331 |
| 5,880,096 A | | 3/1999 | Barrett et al. ............ 514/15 |
| 5,932,549 A | | 8/1999 | Allen et al. ............ 514/18 |
| 6,133,018 A | | 10/2000 | Wu et al. ............ 435/280 |
| 6,133,409 A | | 10/2000 | Salvino et al. ......... 528/363 |
| 6,200,969 B1 | | 3/2001 | Fritz et al. ............ 514/214 |
| 6,242,422 B1 | | 6/2001 | Karanewsky et al. ..... 514/19 |
| 6,291,640 B1 | | 9/2001 | Bailey et al. ........... 530/330 |

FOREIGN PATENT DOCUMENTS

| | | |
|---|---|---|
| JP | 5 32697 | 2/1993 |
| WO | WO 92/02257 | 2/1992 |
| WO | WO 93/23383 | 11/1993 |

OTHER PUBLICATIONS

Schellenberger et al, Theory of Thiamine Pyrophosphate Activity. VIII. Significance of the Intercyclic Methylene Bridge for Thiamine Pyrophosphate Activity, 1988, Hoppe–Seyler's Z. Physiol. Chem., 349(4), pp. 517–518. Abstract Only.*

Greene, Protective Groups in Organic Chemistry, 1986, John Wiley & Sons, New York, pp. 14–16 and 154–159.*

Cagnon et al.; "Unusual Regiochemistry of Cycloaddition of Ketenes to ®–2–tert–Butyldihydrooxazole Derivatives. A Simple Route towards Enantiomerically Pure Functionalised α–Aminocyclobutanones", Tetrahedron Letters, 38(13): 2291–2294, (1997).

Escribano et al.; "(2S,4S)–2–AMINO–4–(2,2–Diphenyl-ethyl) Pentanedioic Acid Selective Group 2 Metabotropic Glutamate Receptor Antagonist", Bioorganic & Medicinal Chemistry Letters 8: 765–770, (1998).

Osborne et al.; "Ligands For Glutamate Receptors: Design and Therapeutic Prospects", Journal of Medicinal Chemistry, 43(14): 2609–2645 (Jul. 13, 2000).

Seebach et al.; 107. Stereoselektive Alkylierung an C(α) von Serin, Glycerinsäure, Threonin und Weinsäure über Heterocyclische Enolate Mit Exocyclischer Doppelbindung $^1)^2$), Helvetica Chimica Acta, 70: 1194–1216, (1987) abstract only.

Wünsch et al.; "Stereoselective Synthese Neuer Zentral Wirksamer Tricyclen Vom Benzomorphan–Typ Mit 2–Phenylethylamin Partialstruktur", Arch. Pharm. (Weinheim)326: 101–113, (1993).

Zhang et al.; "A Teandem Michael Addition Ring–Closure Route to the Metabotropic Receptor Ligand α–(Hydroxymethyl) Glutamic Acid and Its γ–Alkylated Derivatives", J. Org. Chem. 66: 7555–7559 (2001).

International Search Report Completed on Sep. 17, 2002 and Mailed on Oct. 2, 2002.

Renato et al.; "Unusual Regiochemistry of Cycloaddition of Ketenes to (R)–2–tert–Butyldihydrooxazole Derivatives. A Simple Route Towards Emanttiomerically Pure Functionalised α–Aminocyclobutanones", Tetrahedron Lettrers 38 (13): 2291–2294, (1997).

Wünsch et al.; "Stereoselektive Synthese Neuer Zentral Wirksamer Tricyclen Vom Benzomorphan–Typ Mit 2–Phenylethylamin Partialstruktur", Arch. Pharm. (Weinheim) 326:101–113, (1993).

Ezquerra et al.; "Stereoselective Reaction of Lithium Enolates Derived form N–BOC Protected Pyroglutamic Esters", Tetrahedron 49 (38):8665–8678, (1993).

De Blasi et al.; "Molecular Determinants of Metabotropic Glutamate Receptor Signaling", Trends in Pharmacological Sciences 22(3): 114–120, (Mar. 2001).

Nakanishi, S. "Molecular Diversity of Glutamate Receptors and Implications for Brain Function", Science 258: 597–603, (Oct. 23, 1992).

N'Goka et al.; "GABA–Uptake Inhibitors: construction of a General Pharmacophore Model and Successful Prediction of a New Representative", J. Med. Chem. 34: 2547–2557, (1991).

(List continued on next page.)

*Primary Examiner*—Johann Richter
*Assistant Examiner*—Paul A. Zucker
(74) *Attorney, Agent, or Firm*—Dana M. Gordon; Foley Hoag LLP

(57) ABSTRACT

One aspect of the present invention relates to 2-hydroxymethylglutamic acid and congeners thereof. A second aspect of the invention relates to a method of synthesizing 2-hydroxymethylglutamic acid and congeners thereof.

16 Claims, 2 Drawing Sheets

OTHER PUBLICATIONS

Kozikowski et al.; "Synthesis and Biology of the Conformationally Restricted ACPD Analogue, 2–Aminobicyclo[2.1.1]hexane–2,5–dicarboxylic Acid–I, a Potent MGluR Agonist", J. Med. Chem. 41: 1641–1650, (1998).

Escribano et al.; "(2S, 4S)–2–Amino–4–(2,2–Diphenylethyl)Pentanedioic Acid Selective Group 2Metabotropic Glutamate Receptor Antagonist", Bioorganic & Medicinal chemistry Letters 8:765–770, (1998).

Bräuner–Osborne et al.; "Ligands for Glutamate Receptors: Design and Therapeutic Prospects", Journal of Medicinal Chemistry, 43(14):2609–2645, (2000).

* cited by examiner

SYNTHESIS OF 2-HYDROXYMETHYLGLUTAMIC ACID AND CONGENERS THEREOF

RELATED APPLICATIONS

This application claims the benefit of priority to United States Provisional Patent Application serial No. 60/232,275, filed Sep. 13, 2000.

GOVERNMENT SUPPORT

This invention was made with support provided by the National Institutes of Health (Grant number NS 35449); therefore, the government has certain rights in the invention.

BACKGROUND OF THE INVENTION

Glutamic acid is one of the 20 amino acids commonly found in animal proteins. Only the L-stereoisomer occurs in mammalian proteins. Like aspartic acid, glutamic acid has an acidic carboxyl group on its side chain which can serve as both an acceptor and a donor of ammonia, a compound toxic to the body. Once glutamic acid has coupled with ammonia, it is called glutamine and can as such safely transport ammonia to the liver, where the ammonia is eventually converted to urea for excretion by the kidneys. Free glutamic acid (that not incorporated into proteins) can also be converted reversibly to α-ketoglutaric acid, an intermediate in the Krebs cycle, and as such can be degraded to carbon dioxide and water, or transformed into sugars. The acidic side chain of glutamic acid confers one negative charge under most conditions to proteins in which this amino acid is found, thus increasing the water solubility of the protein. Monosodium glutamate (MSG), the monosodium salt of L-glutamic acid, is widely used as a condiment. The amino acid was isolated from wheat gluten in 1866 and chemically synthesized in 1890. It is not essential to the human diet, since it can be synthesized in the body from the common intermediate α-ketoglutaric acid.

The fluid produced by the prostate gland contains significant amounts of glutamic acid, and this amino acid may play a role in normal function of the prostate. In one study, symptoms of benign prostatic hyperplasia (BPH) were improved in a group of forty-five men taking 780 mg of glutamic acid per day for two weeks and then 390 mg for the next two and a half months in combination with equal amounts of the amino acids alanine and glycine, an effect also reported by other researchers. See Damrau, F. "Benign prostatic hypertrophy: Amino acid therapy for symptomatic relief", *J. Am Geriatr Soc* 1962; 10(5):426–30; and Feinblatt, H. M. and Gant, J. C. "Palliative treatment of benign prostatic hypertrophy. Value of glycine-alanine-glutamic acid combination", *J. Maine Med Assoc* March 1958.

L-Glutamate is one of the most abundant excitatory amino acid neurotransmitters found in the mammalian brain. This amino acid acts on diverse glutamate receptors including members of both the ionotropic and metabotropic glutamate receptor (mGluR) families. Bräuner-Osborne, H.; Egebjerg, J.; Nielsen, E.; Madsen, U.; Krogsgaard-Larsen, P. *J. Med. Chem.* 2000, 43, 2609; and Nakanishi, S. *Science* 1992, 258, 597; Blasi, A. D.; Conn, P. J.; Pin, J. P.; Nicoletti, F. *Trends Pharmacol. Sci.* 2001, 22, 114. Because of the possibility to identify ligands that may prove useful in disease intervention, considerable attention has been given to the discovery of both selective agonists and antagonists of these glutamate receptors over the past decade. Mukhopadhyaya, J. K.; Kozikowski, A. P.; Grajkowska, W.; Pshenichkin, S.; Wroblewski, J. T. *Bioorg. Med. Chem. Lett.*, in press; Kozikowski, A. P.; Steensma, D.; Araldi, G. L.; Pshenichkin, S.; Surina, S.; Wroblewski, J. T. *J. Med. Chem.* 1998, 41, 1641.

SUMMARY OF THE INVENTION

One aspect of the present invention relates to 2-hydroxymethylglutamic acid and congeners thereof. A second aspect of the invention relates to a method of synthesizing 2-hydroxymethylglutamic acid and congeners thereof.

DETAILED DESCRIPTION OF THE INVENTION

Figure 1:
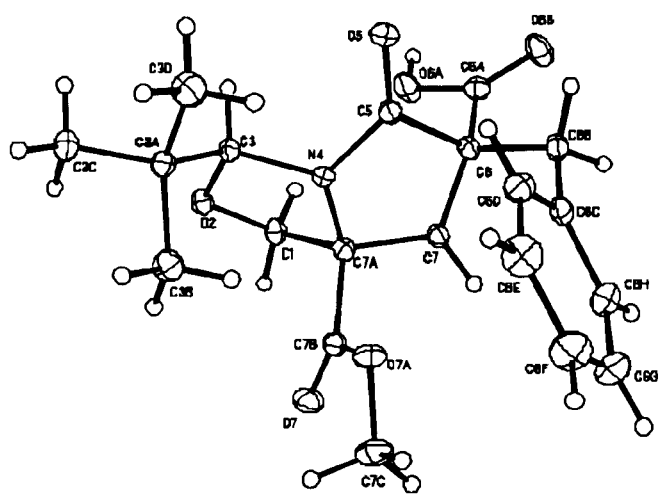
FIG. 1 depicts an ORTEP drawing of the crystal structure of compound 13.

One aspect of the present invention relates to 2-hydroxymethylglutamic acid and congeners thereof. A second aspect of the invention relates to a method of synthesizing 2-hydroxymethylglutamic acid and congeners thereof.

We have discovered that a 2-substituted L-glutamate analogue, namely (2S)-α-(hydroxymethyl)glutamate (1, HMG) is able to act as a relatively potent agonist of the Group 2 receptor mGluR3 while functioning as a weak antagonist at mGluR2. This compound has, in contrast, little or no effect on the Group 1 and Group 3 mGluRs. Generally, the present invention provides an approach to such molecules from D-serine. One aspect of the invention relates to methods by which the parent structure and its congeners, e.g., γ-substituted analogues, may be synthesized. Another aspect of the invention relates to the compounds prepared using these methods.

We have developed a simple Michael addition reaction of the serine-derived oxazolidine 2 (Seebach, D.; Aebi, J. D.; Gander-Coquoz, M.; Naef, R. *Helv. Chim. Acta* 1987, 70, 1194) with ethyl acrylate (Scheme 1). The major product of the reaction was found to be the bicycle 3, which was formed in 27% yield, together with the unsaturated ester 4 in 14% yield. We sought to oxidize intermediate 3 to the corresponding lactam in order to subsequently effect hydrolysis and decarboxylation to afford HMG; however, attempts to bring about this oxidation with either PDC or the Dess-Martin reagent resulted only in formation of the elimination product 4.

Scheme 1

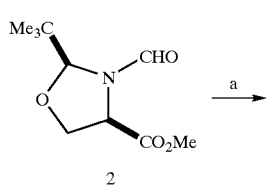

2

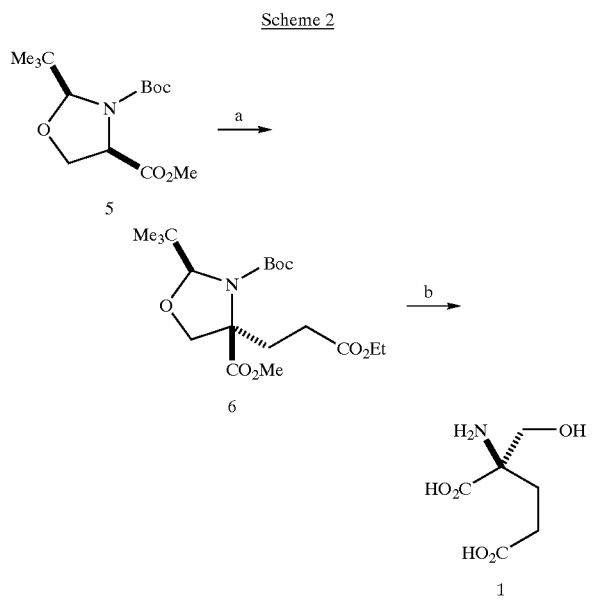

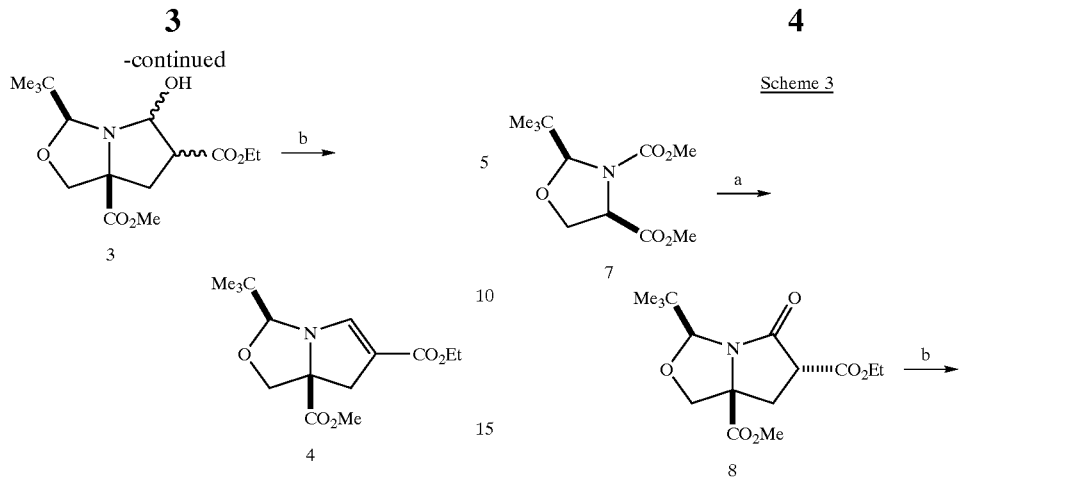

Replacing the N-formyl group of 2 with the larger, less electrophilic Boc protecting group enabled the Michael addition reaction of carbamate 5 (Cagnon, J.; Bideau, F.; Marchand-Brynaert, J.; Ghosez, L. *Tetrahedron Lett.* 1997, 38, 2291) with ethyl acrylate to take place, albeit in very low yield (15% yield based upon 67% conversion). The intermediate 6 was then hydrolyzed with 6 N HCl to afford the required HMG (Scheme 2).

Further, it appeared reasonable to attempt the same reaction using a methoxycarbonyl group for nitrogen protection. The lactam intermediate might in turn allow for the stereocontrolled introduction of additional substituents through further carbanion-based alkylation chemistry. In the event, carbamate 7 (Wuensch, B.; Hoefner, G.; Bauschke, G. *Arch. Pharm.* 1993, 326, 101) was converted to its enolate anion by use of LDA, and the anion reacted in turn with ethyl acrylate (Scheme 3). The desired Michael addition-ring closure was indeed found to take place smoothly to provide the bicycle 8 as a single isomer in 62% yield after recrystallization. The configuration of the newly formed chiral centers were assigned as shown based on an X-ray analysis. Adduct 8 was in turn directly hydrolyzed to the final product HMG in high yield.

Figure 2:
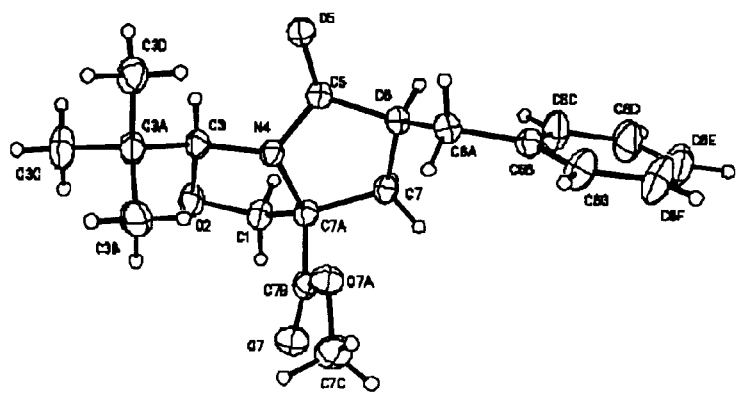
FIG. 2 depicts an ORTEP drawing of the crystal structure of compound 14d.

After successfully obtaining 2-hydroxymethylglutamic acid (HMG), we used the bicycle 8 in the preparation of γ-substituted analogues of HMG. This capability was of interest to us as certain γ-substituted glutamate analogs have been shown to exhibit selective mGluR2 antagonist activity. Escribano, A.; Ezquerra, J.; Pedregal, C.; Rubio, A.; Yruretagoyena, B.; Baker, S. R.; Wright, R. A.; Johnson, B. G.; Schoepp, D. D. *Bioorg. Med. Chem. Lett.* 1998, 8, 765. We found that the best way to carry out this chemistry was to use benzyl acrylate in the tandem reaction to generate the bicycle 9 in 63% yield (Scheme 4). Next, crude 9 was used directly without further purification in an alkylation reaction with either iodomethane or benzyl bromide. In both cases single isomeric products, 10 and 11, respectively, were generated. Hydrogenation of the benzyl esters 10 and 11 afforded the crystalline acids 12 and 13, the structures of which were established by X-ray analysis. As is apparent from FIG. 1, the crystal structure analysis of compound 13 shows that the alkyl substituent has been introduced cis to the methoxycarbonyl group. Next, decarboxylation was brought about by heating the intermediates 12 and 13 at 220° C. for several minutes to afford 14 and 15 as single isomers. See Elsinger, F.; Dauben, W.; Wipke, W. *Org. Synth.*, Coll. Vol. 5, 76 (1973). Decarboxylation occurred with maintenance of the substituent on the convex face of the bicycle as revealed by X-ray analysis (See FIG. 2). Lastly, hydrolysis with 6 N HCl under reflux conditions gave the desired 4-alkylated HMG analogues 15a and 15d. The purity of these compounds was confirmed by their $^1$H NMR spectra.

Scheme 4

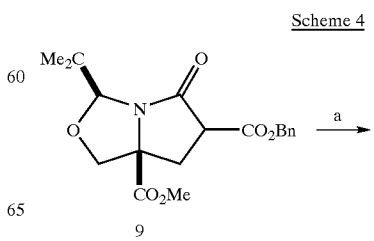

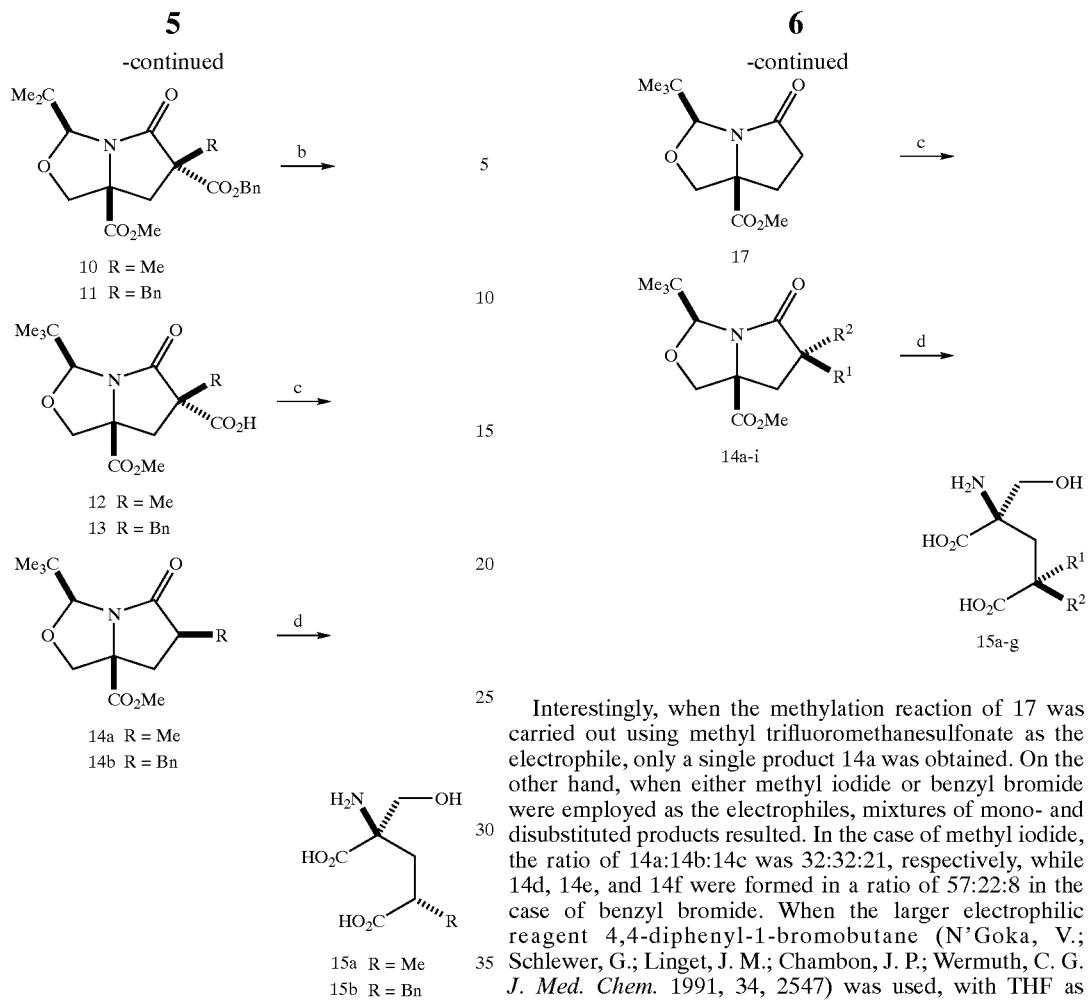

For pharmacological studies, we also wanted access to the 4R- isomers of 15a and 15d in order to ascertain the contribution of this stereocenter to mGluR subtype selectivity and potency. To accomplish this goal, we explored the alkylation chemistry of bicycle 17 which was obtained from 9 by hydrogenation and decarboxylation (Scheme 5).

Scheme 5

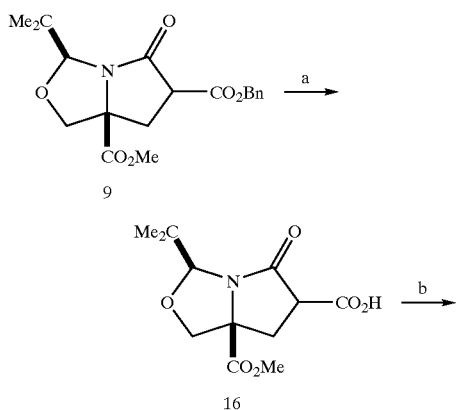

Interestingly, when the methylation reaction of 17 was carried out using methyl trifluoromethanesulfonate as the electrophile, only a single product 14a was obtained. On the other hand, when either methyl iodide or benzyl bromide were employed as the electrophiles, mixtures of mono- and disubstituted products resulted. In the case of methyl iodide, the ratio of 14a:14b:14c was 32:32:21, respectively, while 14d, 14e, and 14f were formed in a ratio of 57:22:8 in the case of benzyl bromide. When the larger electrophilic reagent 4,4-diphenyl-1-bromobutane (N'Goka, V.; Schlewer, G.; Linget, J. M.; Chambon, J. P.; Wermuth, C. G. *J. Med. Chem.* 1991, 34, 2547) was used, with THF as solvent and HMPA as chelating agent (Ezquerra, J.; Pedregal, C.; Rubio, A.; Yruretagoyena, B.; Escribano, A.; Sanchez-Ferrando, F. *Tetrahedron* 1993, 49, 8665), 14 g was obtained in 32% yield, together with a small amount of 14h and 14i (both less than 1% yield). The structures of compounds 14g and 14h were assigned based upon their $^1$H NMR spectra.

As can be seen from Table 1, the proton in α-position to the lactam carbonyl group (7-H) resonates at lower field when it is situated on the convex face of the bicycle. This is observed for 14b and 14e in comparison to 14a and 14d, respectively. As the stereochemistry of these compounds has been firmly established by X-ray analysis, we thus conclude that the alkylation reaction using 4,4-diphenyl-1-bromobutane as the electrophile occurs predominantly on the convex face of the bicycle. The final HMG analogues were obtained from the bicyclic precursors by hydrolysis with 6 N HCl under reflux conditions followed by purification on a $C_{18}$ column.

TABLE 1

$^1$H chemical shifts of the 7-H of the 7-monoalkylated bicyclic compounds.

| Compound | $R^1$ | $R^2$ | δ (7-H) |
|---|---|---|---|
| 14a | Me | H | 2.75 |
| 14b | H | Me | 3.33 |
| 14c | Me | Me | — |

TABLE 1-continued

¹H chemical shifts of the 7-H of the 7-monoalkylated bicyclic compounds.

| Compound | R¹ | R² | δ (7-H) |
|---|---|---|---|
| 14d | Bn | H | 3.00 |
| 14e | H | Bn | 3.51 |
| 14f | Bn | Bn | — |
| 14g | $Ph_2CH(CH_2)_3$ | H | 2.58 |
| 14h | H | $Ph_2CH(CH_2)_3$ | 3.08 |
| 14i | $Ph_2CH(CH_2)_3$ | $Ph_2CH(CH_2)_3$ | — |

Definitions

For convenience, certain terms employed in the specification, examples, and appended claims are collected here.

The abbreviation "HMG" refers to 2-hydroxymethylglutamic acid.

The term "cell surface proteins" includes molecules that occur on the surface of cells, interact with the extracellular environment, and transmit or transduce information regarding the environment intracellularly.

The term "extracellular signals" includes a molecule or a change in the environment that is transduced intracellularly via cell surface proteins that interact, directly or indirectly, with the signal. An extracellular signal is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. Extracellular signals also includes as yet unidentified substances that modulate the activity of a cell surface protein and thereby affect intracellular functions and that are potential pharmacological agents that may be used to treat specific diseases by modulating the activity of specific cell surface receptors.

The term "$ED_{50}$" means the dose of a drug which produces 50% of its maximum response or effect. Alternatively, the dose which produces a predetermined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups (σ([P]=−0.66 for $NH_2$) and positive for electron withdrawing groups (σ[P]=0.78 for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

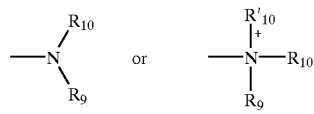

wherein $R_9$, $R_{10}$ and $R'_{10}$ each independently represent a group permitted by the rules of valence.

The term "acylamino" is art-recognized and refers to a moiety that can be represented by the general formula:

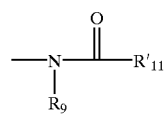

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

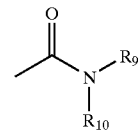

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

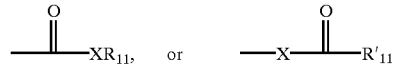

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

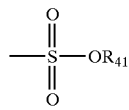

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

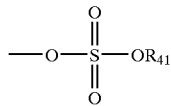

in which $R_{41}$ is as defined above.

The term "sulfonylamino" is art recognized and includes a moiety that can be represented by the general formula:

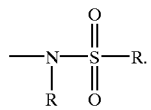

The term "sulfamoyl" is art-recognized and includes a moiety that can be represented by the general formula:

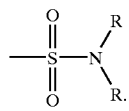

The term "sulfonyl", as used herein, refers to a moiety that can be represented by the general formula:

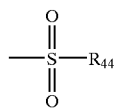

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

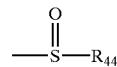

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compounds of the Invention

In certain embodiments, a compound of the present invention is represented by A:

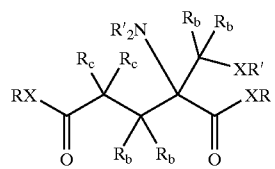

wherein
X represents independently for each occurrence O, NR, or S;
R represents independently for each occurrence H, alkyl, cycloalkyl, aryl, heteroaryl, aralkyl, or heteroaralkyl;
R' represents independently for each occurrence H, alkyl, cycloalkyl, aryl, heteroaryl, aralkyl, heteroaralkyl, formyl, acyl, alkoxycarbonyl, aryloxycarbonyl, aralkoxycarbonyl, or $R_2NC(O)$—;
$R_b$ represents independently for each occurrence H, alkyl, cycloalkyl, aryl, heteroaryl, aralkyl, or heteroaralkyl;
$R_c$ represents independently for each occurrence H, alkyl, cycloalkyl, aryl, heteroaryl, aralkyl, or heteroaralkyl; and
the stereochemical configuration at a stereocenter of a compound represented by A is R, S, or a mixture of these configurations.

In certain embodiments, the compounds of the present invention are represented by A and the attendant definitions, wherein X is O.

In certain embodiments, the compounds of the present invention are represented by A and the attendant definitions, wherein R represents independently for each occurrence H, alkyl, or aralkyl.

In certain embodiments, the compounds of the present invention are represented by A and the attendant definitions, wherein R' represents independently for each occurrence H, alkyl, aralkyl, acyl, alkoxycarbonyl, or aralkoxycarbonyl.

In certain embodiments, the compounds of the present invention are represented by A and the attendant definitions, wherein $R_b$ represents H.

In certain embodiments, the compounds of the present invention are represented by A and the attendant definitions, wherein $R_c$ represents independently for each occurrence H, alkyl, or aralkyl.

In certain embodiments, the compounds of the present invention are represented by A and the attendant definitions, wherein X is O; and R represents independently for each occurrence H, alkyl, or aralkyl.

In certain embodiments, the compounds of the present invention are represented by A and the attendant definitions, wherein X is O; and R' represents independently for each occurrence H, alkyl, aralkyl, acyl, alkoxycarbonyl, or aralkoxycarbonyl.

In certain embodiments, the compounds of the present invention are represented by A and the attendant definitions, wherein X is O; and $R_b$ represents H.

In certain embodiments, the compounds of the present invention are represented by A and the attendant definitions, wherein X is O; and $R_c$ represents independently for each occurrence H, alkyl, or aralkyl.

In certain embodiments, the compounds of the present invention are represented by A and the attendant definitions, wherein X is O; R represents independently for each occurrence H, alkyl, or aralkyl; and R' represents independently for each occurrence H, alkyl, aralkyl, acyl, alkoxycarbonyl, or aralkoxycarbonyl.

In certain embodiments, the compounds of the present invention are represented by A and the attendant definitions, wherein X is O; R represents independently for each occurrence H, alkyl, or aralkyl; R' represents independently for each occurrence H, alkyl, aralkyl, acyl, alkoxycarbonyl, or aralkoxycarbonyl; and $R_b$ represents H.

In certain embodiments, the compounds of the present invention are represented by A and the attendant definitions, wherein X is O; R represents independently for each occurrence H, alkyl, or aralkyl; R' represents independently for each occurrence H, alkyl, aralkyl, acyl, alkoxycarbonyl, or aralkoxycarbonyl; $R_b$ represents H; and $R_c$ represents independently for each occurrence H, alkyl, or aralkyl.

In certain embodiments, the compounds of the present invention are represented by A and the attendant definitions, wherein X is O; R represents H; R' represents H; $R_b$ represents H; and $R_c$ represents independently for each occurrence H, alkyl, or aralkyl.

In certain embodiments, the compounds of the present invention are represented by A and the attendant definitions, wherein said compound is a single enantiomer.

In certain embodiments, the present invention relates to a formulation, comprising a compound represented by A and the attendant definitions; and a pharmaceutically acceptable excipient.

Methods of the Invention

In certain embodiments, the present invention relates to a method depicted in Scheme 1:

Scheme 1

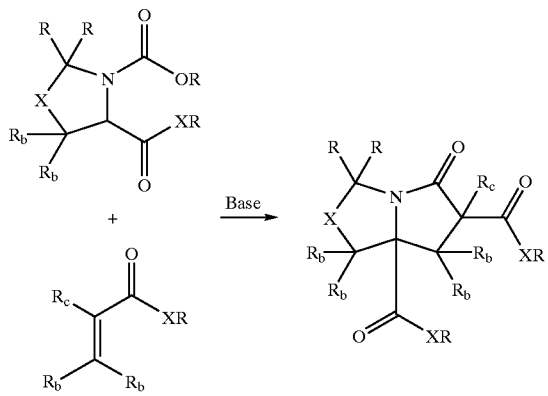

wherein
- X represents independently for each occurrence O, NR, or S;
- R represents independently for each occurrence H, alkyl, cycloalkyl, aryl, heteroaryl, aralkyl, or heteroaralkyl;
- $R_b$ represents independently for each occurrence H, alkyl, cycloalkyl, aryl, heteroaryl, aralkyl, or heteroaralkyl;
- $R_c$ represents independently for each occurrence H, alkyl, cycloalkyl, aryl, heteroaryl, aralkyl, or heteroaralkyl;
- Base is the conjugate base of an alcohol, primary amine, or secondary amine; and
- the stereochemical configuration at a stereocenter of a compound depicted in Scheme 1 is R, S, or a mixture of these configurations.

In certain embodiments, the method of the present invention is represented by Scheme 1 and the attendant definitions, wherein X is O.

In certain embodiments, the method of the present invention is represented by Scheme 1 and the attendant definitions, wherein R represents independently for each occurrence H, alkyl, or aralkyl.

In certain embodiments, the method of the present invention is represented by Scheme 1 and the attendant definitions, wherein $R_b$ represents H.

In certain embodiments, the method of the present invention is represented by Scheme 1 and the attendant definitions, wherein $R_c$ represents independently for each occurrence H, alkyl, or aralkyl.

In certain embodiments, the method of the present invention is represented by Scheme 1 and the attendant definitions, wherein X is O; and R represents independently for each occurrence H, alkyl, or aralkyl.

In certain embodiments, the method of the present invention is represented by Scheme 1 and the attendant definitions, wherein X is O; and $R_b$ represents H.

In certain embodiments, the method of the present invention is represented by Scheme 1 and the attendant definitions, wherein X is O; and $R_c$ represents independently for each occurrence H, alkyl, or aralkyl.

In certain embodiments, the method of the present invention is represented by Scheme 1 and the attendant definitions, wherein X is O; R represents independently for each occurrence H, alkyl, or aralkyl; and $R_b$ represents H.

In certain embodiments, the method of the present invention is represented by Scheme 1 and the attendant definitions, wherein X is O; R represents independently for each occurrence H, alkyl, or aralkyl; $R_b$ represents H; and $R_c$ represents independently for each occurrence H, alkyl, or aralkyl.

In certain embodiments, the method of the present invention is represented by Scheme 1 and the attendant definitions, wherein X is O; R represents H; $R_b$ represents H; and $R_c$ represents independently for each occurrence H, alkyl, or aralkyl.

In certain embodiments, the method of the present invention is represented by Scheme 1 and the attendant definitions, further comprising the step depicted in Scheme 2:

Scheme 2

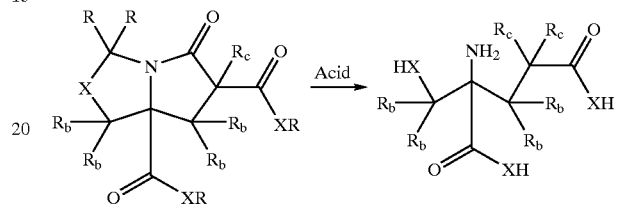

wherein
acid is selected from the group consisting of aqueous HCl, aqueous $HClO_4$, aqueous $H_2SO_4$, and aqueous $H_3PO_4$.

In certain embodiments, the method of the present invention is represented by Scheme 1 and the attendant definitions, further comprising the step depicted in Scheme 3:

Scheme 3

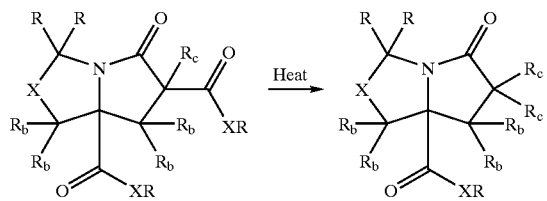

wherein
heat is a temperature in the range from about 100 C. to about 250 C.

In certain embodiments, the method of the present invention is represented by Scheme 3 and the attendant definitions, wherein heat is a temperature in the range from about 200 C. to about 250 C.

In certain embodiments, the method of the present invention is represented by Scheme 1 and the attendant definitions, further comprising the step depicted in Scheme 5:

Scheme 4

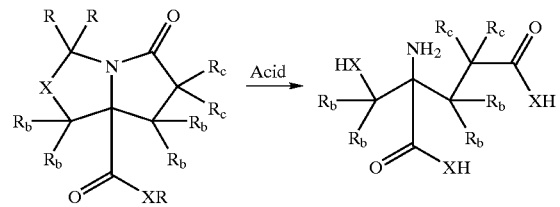

wherein
acid is selected from the group consisting of aqueous HCl, aqueous $HClO_4$, aqueous $H_2SO_4$, and aqueous $H_3PO_4$.

In certain embodiments, the method of the present invention is represented by Scheme 1 and the attendant definitions, further comprising the step depicted in Scheme 5:

Scheme 5

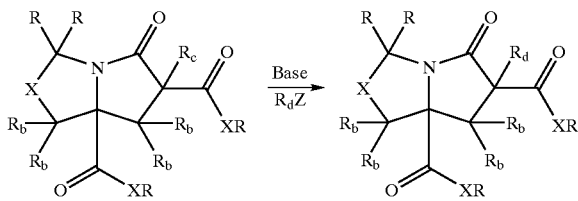

wherein
base is lithium hydride, sodium hydride, or potassium hydride;
$R_d$ represents alkyl, cycloalkyl, aralkyl, or heteroaralkyl; and
Z represents Cl, Br, I, OMs, OTf, or ONf.

In certain embodiments, the method of the present invention is represented by Scheme 5 and the attendant definitions, further comprising the step depicted in Scheme 6:

Scheme 6

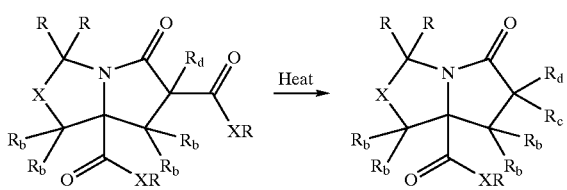

wherein
heat is a temperature in the range from about 100 C. to about 250 C.

In certain embodiments, the method of the present invention is represented by Scheme 6 and the attendant definitions, wherein heat is a temperature in the range from about 200 C. to about 250 C.

In certain embodiments, the method of the present invention is represented by Scheme 3 and the attendant definitions, further comprising the step depicted in Scheme 7:

Scheme 7

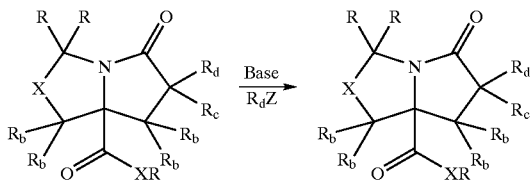

wherein
base is lithium hydride, sodium hydride, or potassium hydride;
$R_d$ represents alkyl, cycloalkyl, aralkyl, or heteroaralkyl; and
Z represents Cl, Br, I, OMs, OTf, or ONf.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and Co., San Francisco, U.S.A., 1969 or "Livestock Feeds and Feeding" O and B books, Corvallis, Oreg., U.S.A., 1977).

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/0805 1, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S.P.A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use of protection/deprotection reactions with photolabile protecting groups.

The key points of this technology are illustrated in Gallop et al. (1994) *J. Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) *PNAS* 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

General Experimental Procedures

THF was freshly distilled under $N_2$ from sodium benzophenone. $^1$H and $^{13}$C NMR spectra were acquired at a proton frequency of 300 MHz, using $CDCl_3$ as solvent unless noted otherwise. $^1$H chemical shifts (ppm) were obtained using $CHCl_3$ ($\delta$=7.26 ppm, for $CDCl_3$ as solvent) or HDO ($\delta$=4.80 ppm, for $D_2O$ as solvent) as internal standards. $^{13}$C chemical shifts were determined with $CHCl_3$ (central peak $\delta$=77.00 ppm, for $CDCl_3$ as solvent) or MeOH ($\delta$=49.15 ppm, for $D_2O$ as solvent) as internal standards. Melting points were determined in Pyrex capillaries with a Thomas-Hoover Unimelt apparatus and are uncorrected. Mass spectra were measured in the EI mode at an ionization potential of 70 eV. X-ray data were collected on a computer-controlled Bruker P4 automatic 4-circle diffractometer. The structures were solved by direct methods and refined, using all independent data, with full matrix least-squares on F2 values using the SHELXTL program package. TLC was performed on Merck silica gel 60F$_{254}$ glass plates. Optical rotations were measured at room temperature.

Example 2

(3S,7aR)-3-tert-Butyl-7,7a-dihydro-1-H-pyrrolo[1,2-c]oxazole-6,7a-dicarboxylic Acid 6-Ethyl Ester 7a-Methyl Ester (4)

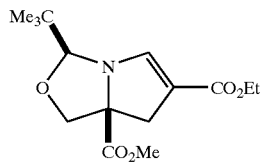

4

To a solution of 2 (350 mg, 1.63 mmol) in THF (6.0 mL) stirred at −78° C. under nitrogen was added a solution of lithium diisopropylamide in THF (0.51 M, 3.4 mL, 1.7 mmol). After the reaction mixture had been stirred at −78° C. for 30 min, ethyl acrylate (188 mg, 1.88 mmol) in THF (2.6 mL) was added, and stirring was continued for 1 h at −78° C. The reaction mixture was poured into $NH_4Cl$ solution and extracted with EtOAc (3×). The organic layers were washed with brine, dried over $Na_2SO_4$, filtered, and concentrated. Purification by flash column chromatography ($SiO_2$, EtOAc/hexane 1:15) afforded unreacted compound 2 (113 mg, 32% recovery) and the products 3 (135 mg, 39% based on 68% conversion) and 4 (70 mg, 21% based on 68% conversion) as colorless oils: Compound 4: $^1$H NMR $\delta$6.82 (s, 1H), 4.70 (d, 1H, J=8.7 Hz), 4.18–4.11 (m, 3H), 3.74 (s, 3H), 3.39 (d, 1H, J=8.7 Hz), 2.84 (br, 2H), 1.25 (t,3H, J=6.9 Hz), 0.87 (s, 9H); $^{13}$C NMR $\delta$172.74, 164.76, 149.77, 110.53, 101.88, 75.41, 71.33, 59.88, 52.59, 34.85, 24.19, 14.38.

Example 3

(2S,4R)-2-tert-Butyl4-[2-(ethoxycarbonyl)ethyl]oxazolidine-3,4-dicarboxylic Acid 3-tert-Butyl Ester 4-Methyl Ester (6)

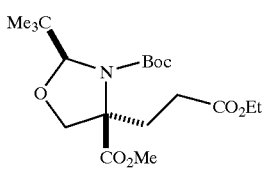

6

To a solution of 5 (550 mg, 1.91 mmol) in THF (10 mL) stirred at −78° C. under nitrogen was added a solution of lithium diisopropylamide in THF (0.53 M, 4.0 mL, 2.1 mmol). After the reaction mixture had been stirred at −78° C. for 30 min, ethyl acrylate (280 mg, 2.80 mmol) in THF (2.5 mL) was added, and stirring was continued for 9 h at −78° C. The reaction mixture was poured into $NH_4Cl$ solution and extracted with EtOAc (3×). The organic layers were washed with brine, dried over $Na_2SO_4$, filtered, and concentrated. Purification by flash column chromatography ($SiO_2$, EtOAc/hexane 1:15) afforded 5 (178 mg, 33% recovery) and the product 6 (75 mg, 15% based on 67% conversion) as a colorless oil: $[\alpha]_D$−50.0° (c 0.5, $CHCl_3$); IR (film) 2961, 1740, 1711 cm$^{-1}$; $^1$H NMR $\delta$5.13 (s, 1H), 4.26

(d, 1H, J=8.7 Hz), 4.13 (q, 2H, J=6.9 Hz), 4.02 (d, 1H, J=8.7 Hz), 3.76 (s, 3H), 2.73 (br, 1H), 2.49 (m, 1H), 2.31 (m, 1H), 2.16 (m, 1H), 1.45 (s, 9H), 1.25 (t, 3H, J=6.9 Hz), 1.00 (s, 9H); $^{13}$C NMR δ172.76, 171.98 153.15 98.12, 81.08, 75.72, 68.10, 60.49, 52.45, 39.49, 30.06, 28.66, 28.01, 26.41, 14.13; MS m/z (%) 330 (6), 230 (100), 184 (46), 57 (95).

Example 4

(3S,7aR)-3-tert-Butyl-1,6,6,7,7a-tetrahydro-5-oxopyrrolo[1,2,-c]oxazole-6,7a-dicarboxylic Acid 6-Ethyl Ester 7a-Methyl Ester (8)

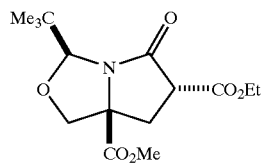

8

To a solution of compound 7 (3.90 g, 15.9 mmol) in 60 mL THF stirred at −78° C. under nitrogen was added a 0.61 M solution of lithium diisopropylamide in THF (31.0 mL, 18.9 mmol, 1.2 equiv). After the reaction mixture had been stirred at −78° C. for 30 min, ethyl acrylate (2.0 g, 20.0 mmol) in THF (10 mL) was added, and stirring was continued for 12 h at −78° C. The reaction mixture was poured into NH$_4$Cl solution and extracted with EtOAc (3×). The organic layers were washed with brine, dried over Na$_2$SO$_4$, filtered, and concentrated. Purification by flash column chromatography (SiO$_2$, EtOAc/hexane 1:10) afforded starting material 7 (1.10 g, 28% recovery) and product 8 (2.92 g, 86% based on 72% conversion). Compound 8: mp 105–107° C. (from acetone/hexane); [α]$_D$-15.2° (c 1.2, MeOH); IR (KBr) 2977, 1732, 1720 cm$^{-1}$; $^1$H NMR δ4.86 (s, 1H), 4.82 (d, 1H, J=8.7 Hz), 4.29–4.15 (m, 3H), 3.77 (s, 3H), 3.54 (d, 1H, J=8.7 Hz), 2.64 (m, 1H), 2.44 (dd, 1H, J=9.0, 13.2 Hz), 1.30 (t, 3H, J=7.2 Hz), 0.85 (s, 9H); $^{13}$ $^{C}$ $^{NMR}$ δ172.94, 172.17, 168.49, 96.59, 73.84, 70.04, 61.94, 52.88, 51.90, 35.78, 33.16, 24.71, 14.15; MS m/z (%) 298 (2), 256 (91), 210 (100). Anal. (C$_{15}$H$_{23}$NO$_6$) Calcd: C, 57.50, H, 7.40; N, 4.47. Found: C, 57.37; H, 7.67; N, 4.41.

Example 5

(3S,6R,7a)-3-tert-Butyl-1,6,7,7a-tetrahydro-6-methyl-5-oxopyrrolo[1,2-c]oxazole-6,7a-dicarboxylic Acid 6-Benzyl Ester 7a-Methyl Ester (10)

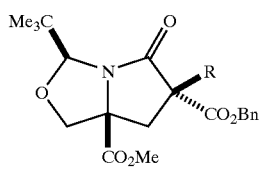

10

R = Me

To a solution of compound 7 (3.60 g, 14.7 mmol) in THF (40 mL) stirred at −78° C. under nitrogen was added a solution of LDA in THF (1.5 M, 12.0 mL, 18.0 mmol). After the reaction mixture had been stirred at −78° C. for 30 min, benzyl acrylate (2.88 g, 17.8 mmol) in THF (10 mL) was added, and stirring was continued for 12 h at −78° C. The reaction mixture was poured into NH$_4$Cl solution and extracted with EtOAc. The combined organic layers were washed with brine, dried over Na$_2$SO$_4$, filtered, and concentrated to afford an inseparable mixture of 7 and 9 (4.80 g).

To a solution of this mixture (95 mg) in DMF (5 mL) was added NaH (60% in oil, 15 mg, 0.38 mmol) under nitrogen. Methyl iodide (40 μL, 0.64 mmol) was added 5 min later. The mixture was stirred overnight, then poured into saturated NH$_4$Cl solution and extracted with EtOAc. The combined organic layers were washed with brine, dried over Na$_2$SO$_4$, filtered, and concentrated. The crude product was purified by column chromatography (SiO$_2$, EtOAc/hexane 1:20) to afford compound 10 as a colorless oil: [α]$_D$-6.0° (c 0.5, CHCl$_3$); IR (film) 2987, 1745 1718 cm$^{-1}$; $^1$H NMR δ7.38–7.28 (m, 5H), 5.23 (d, 1H, J=9.0 Hz), 5.13 (d, 1H, J=9.0 Hz), 4.84 (s, 1H), 4.76 (d, 1H, J=8.7 Hz), 3.78 (s, 3H), 3.47 (d, 1H, J=8.7 Hz), 2.78 (d, 1H, J=14.1Hz), 2.12 (d, 1H, J=14.1 Hz), 1.70 (s, 3H), 0.89 (s, 9H); $^{13}$C NMR δ178.97, 172.71, 171.3 128.64, 128.43, 128.42, 128.02, 98.21, 73.35, 69.79, 67.65, 56.22, 52.86, 38.73, 35.31, 24.82, 21.90; MS m/z (%) 332 (86), 91 (100), 43 (16).

Example 6

(3S,6R,7aR)-6-Benzyl-3-tert-butyl-1,6,7,7a-tetrahydro-5-oxopyrrolo[1,2-c]oxazole-6,7a-dicarboxylic Acid 6-Benzyl Ester 7a-Methyl Ester (11)

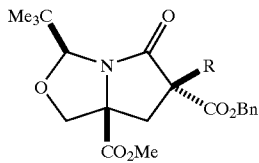

11

R = Bn

To a solution of crude compound 9 (480 mg) in DMF (10 mL) was added NaH (60% in oil, 60 mg, 1.5 mmol) under nitrogen. Benzyl bromide (0.20 mL, 1.7 mmol) was added 5 min later. The mixture was stirred overnight, then poured into saturated NH$_4$Cl solution and extracted with EtOAc. After evaporation, the crude oil was purified by column chromatography (SiO$_2$, hexane/EtOAc 20/1) to afford compound 11 (300 mg) as a colorless oil: [α]$_D$-7.4° (c 2.0, CHCl$_3$); IR (film) 2956, 1742, 1724 cm$^{-1}$; $^1$H NMR δ7.40–7.10 (m, 10H), 5.23 (s, 2H), 4.81 (s, 1H), 4.68 (d, 1H, J=8.4 Hz), 3.56 (s, 3H), 3.52–3.41 (m, 3H), 2.68 (d, 1H, J=8.4 Hz), 2.27 (d, 1H, J 8.4 Hz), 0.88 (s, 9H); $^{13}$C NMR δ177.91, 172.59, 170.39, 135.99, 134.96, 130.24, 128.67, 128.56, 128.40, 127.01, 98.63, 73.08, 69.64, 68.03, 61.19, 52.78, 39.53, 35.27, 33.18, 24.91; MS m/z (%) 450 (0.5), 408 (58), 91 (100).

Example 7

(3S,6R,7aR)-3-tert-Butyl-1,6,7,7a-tetrahydro-6-methyl-5-oxopyrrolo[1,2c]oxazole-6,7a-dicarboxylic Acid 7a-Methyl Ester (12)

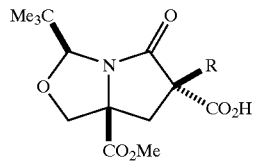

R = Me

To a solution of compound 10 (110 mg, 0.33 mmol) in t-butanol (10 mL) was added 20% Pd(OH)$_2$/C (50 mg), and the mixture was hydrogenated at 1 bar and room temperature overnight. Filtration from the catalyst and concentration afforded the product 12: mp >132° C. (decomp.; from EtOAc/hexane); [α]$_D$–47.4° (c 0.14, CHCl$_3$); IR (KBr) 3118, 2938, 1748, 1716 cm$^{-1}$; $^1$H NMR δ10.0 (br, 1H), 4.85 (s, 1H), 4.82 (d, 1H, J=8.7 Hz), 3.82 (s, 3H), 3.49 (d, 1H, J=8.7 Hz), 2.81 (d, 1H, J=14.4 Hz), 2.25 (d, 1H, J=14.4 Hz), 1.76 (s, 3H), 0.90 (s, 9H); $^{13}$C NMR δ180.10, 174.45, 172.17, 97.88, 73.90, 69.42, 55.33, 53.03, 38.30, 35.33, 24.81, 23.69; MS m/z (%) 255 (0.1), 198 (4), 83 (100).

Example 8

(3S,6R,7aR)-6-Benzyl-3-tert-butyl-1,6,7,7a-tetrahydro-5-oxopyrrolo[1,2-c]oxazole-6,7a-dicarboxylic Acid 7a-Methyl Ester (13)

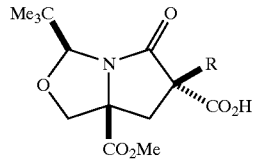

R = Bn

Compound 11 (250 mg, 0.54 mmol) was dissolved in t-butanol (10 mL), then 20% Pd(OH)$_2$/C (90 mg) was added, and the mixture was hydrogenated at 1 bar and room temperature overnight. The catalyst was filtered off, and the solvent was removed under vacuum to give the product 13 (200 mg, 100%): mp >133° C. (decomp.; from hexane/EtOAc); [α]$_D$+9.1° (c 0.4 CHCl$_3$); IR (KBr) 3141, 2973, 1736, 1718 cm$^{-1}$; $^1$H NMR δ7.33–7.14 (m, 5H), 6.5 (br, 1H), 4.84 (s, 1H), 4.80 (d, 1H, J=8.7 Hz), 3.77 (s, 3H), 3.54–3.38 (m, 3H), 2.67 (d, 1H, J=14.7 Hz ), 2.43 (d, 1H, J=14.7 Hz), 0.93 (s, 9H); $^{13}$C NMR δ179.77, 172.03, 171.80, 134.52, 130.02, 128.50, 127.70, 97.94, 74.25, 69.22, 60.24, 53.09, 42.94, 35.34, 35.15, 24.93; MS m/z (%) 331 (0.3), 274 (36), 58 (72), 43 (100). Anal. (C$_{20}$H$_{25}$NO$_6$) Calcd: C, 63.99; H, 6.71; N, 3.73. Found; C, 64.33; H, 6.47; N, 3.57.

Example 9

(3S,7aR)-3-tert-Butyl-1,6,7,7a-tetrahydro-5-oxopyrrolo[1,2-c]oxazole-7a-carboxylic Acid Methyl Ester (17)

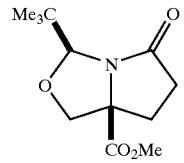

To a solution of crude compound 9 (1.35 g) in t-butanol (15 mL) was added 20% Pd(OH)$_2$/C (0.45 g), and the mixture was hydrogenated at 1 bar and room temperature for 1 h. Filtration from the catalyst and concentration afforded the crude acid 16, which was heated to 220° C. for 5 min. The crude product was purified by column chromatography (SiO$_2$, hexane/EtOAc 10/1) to afford the bicycle 17 (650 mg, 75% over 2 steps): mp 82–83° C. (from EtOAc/hexane); [α]$_D$–50.2° (c 2.0, CHCl$_3$); IR (KBr) 2965, 1741, 1708 cm$^{-1}$; $^1$H NMR δ4.87 (s, 1H), 4.81 (d, 1H, J 8.4 Hz), 3.79 (s, 3H), 3.44 (d, 1H, J=8.4 Hz), 3.10 (m, 1H), 2.52 (m, 1H), 2.32 (m, 1H), 2.16 (m, 1H), 0.88 (s, 9H); $^{13}$C NMR δ178.42, 172.77, 96.43, 73.97, 72.01, 52.65, 35.72, 34.40, 29.68, 24.74; MS m/z (%) 226 (0.3), 184 (22), 58 (30), 43 (100). Anal. (C$_{13}$H$_{21}$NO$_4$) Calcd: C, 59.73; H, 7.94; N, 5.81. Found: C, 59.62; H, 7.84; N, 5.61.

Example 10

Representative Procedure for the Alkylation of Bicycle 17

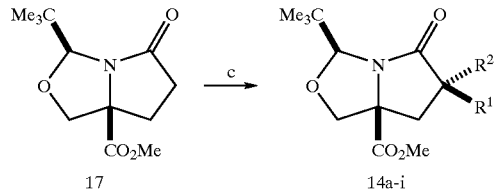

To a solution of compound 17 (146 mg, 0.61 mmol) in THF (7 mL), which was stirred at –78° C., was added a solution of LDA in THF (1.0 M, 0.8 mL, 0.8 mmol). After the reaction mixture had been stirred at –78° C. for 1 h, iodomethane (45 μL, 0.73 mmol) was added, and stirring was continued for 3 h. The reaction mixture was quenched with saturated NH$_4$Cl solution (20 mL) at –78° C. and extracted with diethyl ether (3×20 mL). The combined organic phases were dried over Na$_2$SO$_4$, filtered, and concentrated. Column chromatogaphy (SiO$_2$, hexane/EtOAc 10/1) afforded the products 14a (50 mg, 32%), 14b (50 mg, 32%), and 14c (35 mg, 22%).

(3S,6S,7aR)-3-tert-Butyl-1,6,7,7a-tetrahydro-6-methyl-5-oxopyrrolo[1,2-c]oxazole-7a -carboxylic Acid Methyl Ester (14a): mp 107–108° C. (from EtOAc/hexane); [α]$_D$–58.3° (c 0.42, CHCl$_3$); IR (KBr) 2956, 1738, 1707 cm$^{-1}$; $^1$H NMR δ4.81 (s, 1H), 4.79 (d, 1H, J=9.0 Hz), 3.78 (s, 3H), 3.31 (d, 1H, J=9.0 Hz), 2.75 (m, 1H), 2.39 (dd, 1H, J=10.8, 13.8 Hz), 1.95 (dd, 1H, J=10.8, 13.8 Hz), 1.43 (d, 3H, J=7.8 Hz), 0.89 (s, 9H); $^{13}$C NMR δ183.32, 173.20, 97.70, 73.52, 70.85, 52.62, 40.19, 35.27, 34.61, 24.82, 18.41; MS m/z (%)

240 (0.6), 198 (40), 58 (72), 43 (100). Anal. ($C_{13}H_{21}NO_4$) Calcd: C, 61.16; H, 8.29; N, 5.49. Found: C, 61.11; H, 8.31; N, 5.31.

(3S,6R,7aR)-3-tert-Butyl-1,6,7,7a-tetrahydro-6-methyl-5-oxopyrrolo[1,2-c]oxazole-7a-carboxylic Acid Methyl Ester (14b): $[\alpha]_D$ −27.1° (c 0.76, CHCl$_3$); IR (film) 2961, 1743, 1718 cm$^{-1}$; $^1$H NMR δ4.87 (s, 1H), 4.82 (d, 1H, J=8.7 Hz), 3.78 (s, 3H), 3.40 (d, 1H, J 8.7 Hz), 3.33 (m, 1H), 2.54 (dd, 1H, J=8.7, 13.2 Hz), 1.78 (dd, 1H, J=8.7, 13.2 Hz), 1.18 (d, 3H, J=6.9 Hz), 0.88 (s, 9H); $^{13}$C NMR δ180.01, 172.78, 96.19, 74.71, 69.61, 52.64, 39.85, 39.46, 35.81, 24.75, 14.92; MS m/z (%) 256 (0.3), 198 (100), 138 (40). Anal. ($C_{13}H_{21}NO_4$) C 61.16; H, 8.29; N, 5.49. Found: C, 60.96; H, 8.45; N, 5.27.

(3S,7aR)-3-tert-Butyl-1,6,7,7a-tetrahydro-6,6-dimethyl-5-oxopyrrolo [1,2-c]oxazole-7 a-carboxylic Acid Methyl Ester (14c): $[\alpha]_D$ −28.5° (c 0.80, CHCl$_3$); IR (film) 2965, 1744, 1718 cm$^{-1}$; $^1$H NMR δ4.84 (s, 1H), 4.81 (d, 1H, J=8.7 Hz), 3.78 (s, 3H), 3.28 (d, 1H, J=8.7 Hz), 2.20 (d, 1H, J=14.1 Hz), 2.05 (d, 1H, J=14.1 Hz), 1.42 (s, 3H), 1.20 (s, 3H), 0.90 (s, 9H); $^{13}$C NMR δ184.62, 173.23, 97.52, 75.20, 68.67, 52.60, 44.98, 43.08, 35.34, 27.09, 26.59, 24.90; MS m/z (%) 270 (0.1), 212 (34), 58 (79), 43 (100).

Compounds 14d–f were obtained analogously in yields of 57%, 22%, and 8%, respectively. Compound 14d can also be prepared in 91% yield by heating acid 13 to 220° C. under nitrogen for 5 min.

(3S,6S,7aR)-6-Benzyl-3-tert-butyl-1,6,7,7a-tetrahydro-5-oxopyrrolo[1,2-c]oxazole-7a-carboxylic Acid Methyl Ester (14d): mp 130–131° C. (from EtOAc/hexane); $[\alpha]_D$+32.9° (c 0.90, CHCl$_3$); IR (KBr) 2977, 1736, 1706 cm$^{-1}$; $^1$H NMR δ7.39–7.18 (m, 5H), 4.88 (s, 1H), 4.78 (d, 1H, J=8.7 Hz), 3.80 (s, 3H), 3.32 (d, 1H, J=8.7 Hz), 3.30 (br, 1H), 3.11–297 (m, 2H), 2.20–2.02 (m, 2H), 0.94 (s, 9H); $^{13}$C NMR δ181.68, 172.97, 138.69, 128.79, 128.53, 128.36, 126.49, 97.61, 73.53, 70.73, 52.59, 47.13, 37.97, 35.25, 31.31, 24.81; MS m/z (%) 331 (0.1), 316 (1), 274 (48), 43 (100). Anal. ($C_{19}H_{25}NO_4$) Calcd: C, 68.86; H, 7.60; N, 4.23. Found: C, 68.55; H, 7.23; N, 4.00.

(3S,6R,7aR)-6-Benzyl-3-tert-butyl-1,6,7,7a-tetrahydro-5-oxopyrrolo[1,2-c]oxazole-7a-carboxylic Acid Methyl Ester (14e): $[\alpha]_D$−28.8° (c 0.16, CHCl$_3$); IR (film) 2957, 1740, 1705 cm$^{-1}$;$^1$ H NMR δ7.32–7.15 (m, 5H), 4.88 (s, 1H), 4.76 (d, 1H, J=8.7 Hz), 3.73 (s, 3H) 3.51 (m, 1H), 3.29–3.23 (m, 2H), 2.63 (m, 1H), 2.32 (m, 1H), 1.85 (t, 1H, J=12.6 Hz), 0.89 (s, 9H); $^{13}$C NMR δ178.67, 172.55, 138.78, 128.87, 128.57, 126.47, 96.29, 74.53, 69.64, 52.65, 46.70, 36.76, 36.25, 35.79, 24.76; MS m/z (%) 331 (0.4), 274 (100), 91 (29), 43 (32). Anal. ($C_{19}H_{25}NO_4$) Calcd: C, 68.86; H, 7.60; N, 4.23. Found: C, 68.51; H, 7.21; N, 3.90.

(3S,7aR)-6,6-Dibenzyl-3-tert-butyl-1,6,7,7a-tetrahydro-5-oxopyrrolo[1,2-c]oxazole-7a-carboxylic Acid Methyl Ester (14f): $[\alpha]_D$−5.4° (c 0.28, CHCl$_3$); IR (film) 3028, 2957, 1742, 1712, 1732, 1720 cm$^{-1}$; $^1$H NMR δ7.36–7.09 (m, 1OH), 4.60 (s, 1H), 4.24 (d, 1H, J=8.4 Hz), 3.59 (s, 3H), 3.35 (d, 1H, J=13.5 Hz), 3.30 (d, 1H, J=13.2 Hz), 3.01 (d, 1H J=1.32 Hz), 2.48 (d, 1H, J=13.5 Hz), 2.18 (d, 1H, J=14.1 Hz), 2.05 (d, 1H, J=14.1 Hz), 1.68 (d, 1H, J=8.4 Hz), 0.85 (s, 9H); $^{13}$C NMR δ183.04, 173.34, 137.30, 136.74, 130.86, 130.81, 128.52, 128.25, 127.17, 126.89, 97.31, 72.27, 68.60, 55.43, 52.63, 45.05, 42.13, 35.22, 32.02, 24.93; MS m/z (%) 406 (1), 364 (100), 91 (54), 43 (49).

Preparation of Compounds 14g–i. To a solution of bicycle 17 (260 mg, 1.08 mmol) in THF (7.0 mL) under nitrogen were added at −78° C. successively a solution of LDA (1.5 M, 1.0 mL) and HMPA (1.0 mL). After 1 h, 4-bromo-1,1-diphenylbutane (360 mg, 1.25 mmol) in THF (3.0 mL) was added. After 6 h at −78° C., the reaction mixture was quenched with saturated NH$_4$Cl solution. The product was extracted into EtOAc, and the combined organic layers were washed with brine, dried (Na$_2$SO$_4$), and concentrated under reduced pressure. Separation by column chromatography (SiO$_2$, hexane/EtOAc 30:1) afforded starting material 17 (140 mg, 54% recovery) and compound 14g (70 mg, 31%) besides traces of 14h (2 mg) and 14i (2 mg).

(3S,6S,7aR)-3-tert-Butyl-6-(4,4-diphenylbutyl)-1,6,7,7a-tetrahydro-5-oxopyrrolo[1,2c]oxazole-7a-carboxylic Acid Methyl Ester (14g): colorless oil; $[\alpha]_D$−19.0° (c 0.28, CHCl$_3$); IR (film) 2954, 1742, 1713 cm$^{-1}$; $^1$H NMR δ7.30–7.15 (m, 10H), 4.80 (s, 1H), 4.76 (d, 1H, J=8.4 Hz), 3.92 (t, 1H, J=4.8 Hz), 3.73 (s, 3H), 3.26 (d, 1H, J=8.4 Hz), 2.58 (m, 1H), 2.28–1.69 (m, 6H), 1.42–1.32 (m, 2H), 0.88 (s, 9H); $^{13}$C NMR δ182.81, 173.18, 144.90, 144.76, 128.41, 127.78, 127.74, 126.13, 126.10, 97.90, 73.39, 70.83, 52.60, 50.93, 45.13, 35.21, 32.70, 32.40, 25.76, 24.86; MS m/z (%) 449 (6), 392 (100), 91 (16), 43 (18).

(3S,6R,7aR)-3-tert-Butyl-6-(4,4-diphenylbutyl)-1,6,7,7a-tetrahydro-5-oxopyrrolo[1,2-c]oxazole-7a-carboxylic Acid Methyl Ester (14h): colorless oil; $[\alpha]_D$−29.6° (c 0.5, CHCl$_3$); $^1$H NMR δ7.30–7.14 (m, 10H), 4.84 (s, 1H), 4.78 (d, 1H, J=8.7 Hz), 3.89 (t, 1H, J=7.8 Hz), 3.75 (s, 3H), 3.33 (d, 1H, J=8.7 Hz), 3.08 (m, 1H), 2.38 (m 1H), 2.11–1.24 (m, 7NMR δ179.48, 172.76, 144.91, 128.44, 127.79, 127.74, 126.16, 126.13, 96.23, 74.67, 69.76, 52.68, 51.07, 44.93, 37.54, 35.83, 35.47, 30.36, 25.66, 24.78; MS m/z (%) 449 (6), 392 (94), 43 (18).

(3S,7aR)-3-tert-Butyl-6,6-bis(4,4-diphenylbutyl)-1,6,7,7a-tetrahydro-5-oxopyrrolo[1,2-c]oxazole-7a-carboxylic Acid Methyl Ester (14i): colorless oil; $[\alpha]_D$−15.5° (c 1.2, CHCl$_3$); IR (film) 2953, 1742, 1714 cm$^1$; $^1$H NMR δ7.29–7.12 (m, 20H), 4.67 (s, 1H), 4.63 (d, 1H, J=8.4 Hz), 3.89 (t, 1H, J=8.1 Hz), 3.83 (t, 1H, J=8.1 Hz), 3.63 (s, 3H), 3.01 (d, 1H, J=8.4 Hz), 2.03–0.96 (m, 14H), 0.84 (s, 9H); $^{13}$C NMR δ183.82, 173.26, 144.94, 144.92, 144.74, 144.72, 128.41, 128.40, 127.80, 127.77, 127.75, 126.15, 126.14, 126.07, 97.50, 74.11, 68.67, 52.42, 52.00, 50.85, 50.77, 37.79, 37.30, 35.86, 35.78, 35.74, 35.19, 24.93, 23.03, 22.39; MS m/z (%) 657 (5), 600 (45), 572 (12), 44 (100).

Example 11

Representative Procedure for Hydrolysis: (R)-2 (Hydroxymethyl)glutamic acid (1)

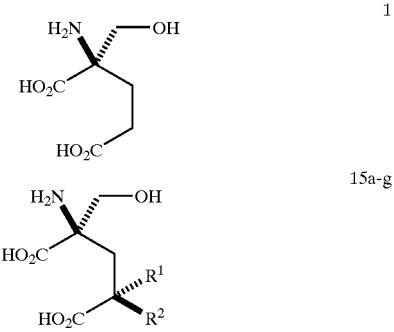

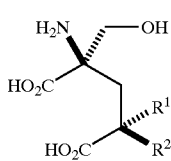

15a-g

A solution of compound 8 (930 mg, 2.97 mmol) in 6 N HCl (20 mL) was stirred under reflux overnight, then concentrated. Purification by reverse phase column chromatography ($C_{18}$, 125 Å, Waters; $H_2O$ as eluent) and lyophilization afforded HMG (1; 580 mg, 91%): $[\alpha]_D$ −1.6° (c 1.0, $H_2O$); $^1H$ NMR ($D_2O$) δ4.02 (d, 1H, J=12.3 Hz), 3.75 (d, 1H, J=12.3 Hz), 2.61–2.43 (m, 2H), 2.23–2.06 (m, 2H); $^{13}C$ NMR ($D_2O$) δ176.13, 171.58, 64.35, 63.45, 28.15, 26.86. Anal. ($C_6H_{11}NO_5 \cdot HCl \cdot \frac{1}{2}H_2O$) Calcd: C, 32.37; H, 5.89; N, 6.29. Found: C, 32.22; H, 5.74; N 6.16

The following compounds were obtained analogously:

(2R,4S)-2-(Hydroxymethyl)-4-methylglutamic Acid (15a): $[\alpha]_D$ −18.2° (c 0.34, $CH_3OH$); IR (KBr) 3407, 1683 cm$^{-1}$; $^1H$ NMR ($D_2O$) δ3.90 (d, 1H, J=11.7 Hz), 3.70 (d, 1H, J=11.7 Hz), 2.69 (m, 1H), 2.44 (dd, 1H, J=9.3, 13.8 Hz), 1.96 (dd, 1H, J=9.3, 13.8 Hz), 1.14 (d, 3H, J=7.2 Hz); $^{13}C$ NMR ($CD_3OD$) δ182.62, 176.34, 67.93, 67.05, 37.47, 37.08, 17.16. Anal. ($C_7H_{13}NO_5 \cdot 1.4HCl$) Calcd: C, 34.71; H, 5.99; N, 5.78. Found: C, 34.70; H, 5.59; N, 5.57.

(2R,4R)-2-(Hydroxymethyl)-4-methylglutamic Acid (15b): $[\alpha]_D$ +8.9° (c 0.18, $CH_3OH$); $^1H$ NMR ($D_2O$) δ3.94 (d, 1H, J=11.7 Hz), 3.64 (d, 1H, J=11.7 Hz), 2.67 (m, 1H), 2.55 (dd, 1H, J=9.0, 12.6 Hz), 1.78 (dd, 1H, J=9.0, 12.6 Hz), 1.14 (d, 3H, J=7.2 Hz); $^{13}C$ NMR($D_2O$) δ183.82, 177.99, 67.03, 66.20, 35.89, 35.51, 15.55.

(R)-2-(Hydroxymethyl)-4,4-dimethylglutamic Acid (15c): $[\alpha]_D$ −18.5° (c 0.13, MeOH); $^1H$ NMR ($D_2O$) δ3.93 (d, 1H, J=11.4 Hz), 3.64 (d, 1H, J=11.4 Hz), 2.28 (d, 1H, J=13.8 Hz), 2.05 (d, 1H, J=13.8 Hz), 1.16 (s, 3H), 1.13 (s, 3H); $^{13}C$ NMR ($D_2O$) δ188.10, 179.55, 68.88, 67.42, 43.73, 43.06, 27.66, 27.19. Anal. ($C_8H_{15}NO_5 \cdot 0.5HCl$) Calcd: C, 43.00; H, 6.99; N, 6.27. Found: C, 42.72; H, 6.34; N, 6.06.

(2R,4S)-4-Benzyl-2-(hydroxymethyl)glutamic Acid (15d): $[\alpha]_D$ +70.4° (c 0.16, $CH_3OH$) IR (KBr) 3363, 1683 cm$^{-1}$; $^1H$ NMR ($D_2O$) δ7.36–7.24 (m, 5H), 3.81 (d, 1H, J=11.7 Hz), 3.62 (d, 1H, J=11.7 Hz), 3.12–2.92 (m, 2H), 2.77 (m, 1H), 2.23–2.05 (m, 2H). Anal. ($C_{13}H_{17}NO_5 \cdot 0.7H_2O \cdot 0.1HCl$) Calcd: C, 55.07; H, 6.58; N, 4.94. Found: C, 54.96; H, 6.68; N, 4.49.

(2R,4R)-4-Benzyl-2-(hydroxymethyl)glutamic Acid (15e): $[\alpha]_D$ −33.9° (c 0.13, MeOH); IR (KBr) 3386, 1701, 1664 cm$^{-1}$; $^1H$ NMR ($D_2O$) δ7.40–7.27 (m, 5H), 3.77 (d, 1H, J=11.7 Hz), 3.24 (d, 1H, J=11.7 Hz), 3.09–2.96 (m, 2H), 2.80 (m, 1H), 2.33 (m, 1H), 1.85 (m, 1H); $^{13}C$ NMR ($D_2O$) δ184.14, 178.85, 140.94, 131.74, 131.16, 129.20, 69.49, 68.17, 44.39, 37.91, 33.99.

(R)-4,4-Dibenzyl-2-(hydroxymethyl)glutamic Acid (15f): $[\alpha]_D$ −8.2° (c 0.12, MeOH); IR (film) 3415, 1682 cm$^{-1}$; $^1H$ NMR ($CD_3OD$) δ7.25–7.13 (m, 10H), 3.16 (d, 1H, J=10.5 Hz), 13.5 (d, 1H, J=13.5 Hz), 3.01 (d, 1H, J=13.2 Hz), 2.65 (d, 1H, J=13.2 Hz), 2.53 (d, 1H, J=13.5 Hz), 2.32 (d, 1H, J=14.7 Hz), 2.19 (d, 1H, J=10.5 Hz), 1.80 (d, 1H, J=14.7 Hz); $^{13}C$ NMR ($CD_3OD$) δ181.92, 175.97, 138.85, 138.02, 131.90, 131.80, 129.56, 129.53, 128.13, 128.11, 69.44, 65.46, 52.65, 45.31, 44.03, 33.25. Anal. ($C_{20}H_{23}NO_5 \cdot 1.7HCl$) Calcd: C, 57.28; H, 5.70; N, 3.34. Found: C, 57.31; H, 5.62; N, 3.03.

(2R,4S)-4-(4,4-Diphenylbutyl)-2-(hydroxymethyl)glutamic Acid (15g): $[\alpha]_D$ −9.5° (c 0.2, MeOH); $^1H$ NMR ($CD_3OD$) δ7.25–7.09 (m, 10H), 3.91 (t, 1H, J=7.8 Hz), 3.68 (d, 1H, J=11.1 Hz), 3.61 (d, 1H, J=11.1 Hz), 2.45 (m, 1H), 2.28 (m, 1H), 2.11–2.01 (m, 2H), 1.89–1.78 (m, 2H), 1.42–1.27 (m, 3H); $^{13}C$ NMR ($CD_3OD$) δ181.80, 180.02, 146.82, 146.78, 129.54, 129.52, 129.05, 129.02, 127.18, 127.16, 68.84, 68.52, 52.63, 43.16, 36.77, 35.95, 32.71, 27.01.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by A:

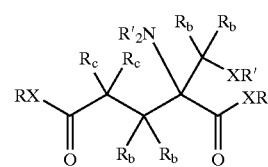

A wherein
  X represents independently for each occurrence O, NR, or S;
  R represents independently for each occurrence H, alkyl, cycloalkyl, aryl, heteroaryl, aralkyl, or heteroaralkyl;
  R' represents independently for each occurrence H, alkyl, cycloalkyl, aryl, heteroaryl, aralkyl, heteroaralkyl, formyl, acyl, alkoxycarbonyl, aryloxycarbonyl, aralkoxycarbonyl, or $R_2NC(O)$—;
  R" represents independently for each occurrence H, cycloalkyl, aryl, heteroaryl, aralkyl, heteroaralkyl, formyl, acyl, alkoxycarbonyl, aryloxycarbonyl, aralkoxycarbonyl, or $R_2NC(O)$—;
  $R_b$ represents independently for each occurrence H, alkyl, cycloalkyl, aryl, heteroaryl, aralkyl, or heteroaralkyl;
  $R_c$ represents independently for each occurrence H, alkyl, cycloalkyl, aryl, heteroaryl, aralkyl, or heteroaralkyl; and
  the stereochemical configuration at a stereocenter of a compound represented by A is R, S, or a mixture of these configurations.

2. The compound of claim 1, wherein X is O.

3. The compound of claim 1, wherein R represents independently for each occurrence H, alkyl, or aralkyl.

4. The compound of claim 1, wherein R' represents independently for each occurrence H, alkyl, aralkyl, acyl, alkoxycarbonyl, or aralkoxycarbonyl.

5. The compound of claim 1, wherein $R_b$ represents H.

6. The compound of claim 1, wherein $R_c$ represents independently for each occurrence H, alkyl, or aralkyl.

7. The compound of claim 1, wherein X represents independently for each occurrence O; and
  R represents independently for each occurrence H, alkyl, or aralkyl.

8. The compound of claim 1, wherein X represents independently for each occurrence O; and R' represents independently for each occurrence H, alkyl, aralkyl, acyl, alkoxycarbonyl, or aralkoxycarbonyl.

9. The compound of claim 1, wherein X represents independently for each occurrence O; and $R_b$ represents H.

10. The compound of claim 1, wherein X represents independently for each occurrence O; and $R_c$ represents independently for each occurrence H, alkyl, or aralkyl.

11. The compound of claim 1, wherein X represents independently for each occurrence O;

R represents independently for each occurrence H, alkyl, or aralkyl; and

R' represents independently for each occurrence H, alkyl, aralkyl, acyl, alkoxycarbonyl, or aralkoxycarbonyl.

12. The compound of claim 1, wherein X represents independently for each occurrence O;

R represents independently for each occurrence H, alkyl, or aralkyl;

R' represents independently for each occurrence H, alkyl, aralkyl, acyl, alkoxycarbonyl, or aralkoxycarbonyl; and $R_b$ represents H.

13. The compound of claim 1, wherein X represents independently for each occurrence O;

R represents independently for each occurrence H, alkyl, or aralkyl;

R' represents independently for each occurrence H, alkyl, aralkyl, acyl, alkoxycarbonyl, or aralkoxycarbonyl;

$R_b$ represents H; and $R_c$ represents independently for each occurrence H, alkyl, or aralkyl.

14. The compound of claim 1, wherein X represents independently for each occurrence O;

R represents H;

R' represents H;

R" represents H;

$R_b$ represents H; and $R_c$ represents independently for each occurrence H, alkyl, or aralkyl.

15. The compound of claim 1, wherein said compound is a single enantiomer.

16. A formulation, comprising a compound of claim 1; and a pharmaceutically acceptable excipient.

* * * * *